(12) United States Patent
Kaasa et al.

(10) Patent No.: US 9,090,813 B2
(45) Date of Patent: Jul. 28, 2015

(54) PROCESS FOR HYDRATE INHIBITOR REGENERATION

(75) Inventors: Baard Kaasa, Stavanger (NO); Per Halvard Billington, Slependen (NO)

(73) Assignee: STATOIL PETROLEUM AS, Stavanger (NO)

( * ) Notice: Subject to any disclaimer, the term of this patent is extended or adjusted under 35 U.S.C. 154(b) by 445 days.

(21) Appl. No.: 13/146,388

(22) PCT Filed: Jan. 22, 2010

(86) PCT No.: PCT/GB2010/000102
§ 371 (c)(1),
(2), (4) Date: Oct. 12, 2011

(87) PCT Pub. No.: WO2010/084323
PCT Pub. Date: Jul. 29, 2010

(65) Prior Publication Data
US 2012/0018293 A1    Jan. 26, 2012

(30) Foreign Application Priority Data

Jan. 26, 2009   (GB) .................................. 0901254.3

(51) Int. Cl.
*C07C 29/80*    (2006.01)
*C09K 8/52*     (2006.01)

(52) U.S. Cl.
CPC . *C09K 8/52* (2013.01); *C07C 29/80* (2013.01); *C09K 2208/22* (2013.01)

(58) Field of Classification Search
CPC ....... C09K 8/52; C09K 2208/22; C07C 29/80
USPC .................. 203/12, 18; 568/854, 868, 913
See application file for complete search history.

(56) References Cited

U.S. PATENT DOCUMENTS

| 4,332,643 A | 6/1982 | Reid |
| 5,817,889 A | 10/1998 | Pondebat et al. |

(Continued)

FOREIGN PATENT DOCUMENTS

| GB | 2334460 A | 8/1999 |
| WO | 98/48920 A1 | 11/1998 |

(Continued)

OTHER PUBLICATIONS

International Search Report and Written Opinion for International Application No. PCT/GB2010/000102 dated Jul. 16, 2010.

*Primary Examiner* — Jafar Parsa
*Assistant Examiner* — Medhanit Bahta
(74) *Attorney, Agent, or Firm* — Knobbe, Martens, Olson & Bear, LLP

(57) ABSTRACT

The invention provides a process for the production of a lean liquid hydrate inhibitor composition from a rich liquid hydrate inhibitor composition in which the liquid hydrate inhibitor has a boiling point above that of water, which process comprises: (a) feeding said rich liquid hydrate inhibitor composition to a first distillation vessel; (b) withdrawing a water and inhibitor containing vapor from said first distillation vessel and feeding it to a second distillation vessel; (c) withdrawing water vapor from said second distillation vessel; (d) withdrawing a lean hydrate inhibitor composition from said second distillation vessel in liquid form; (e) withdrawing a lean hydrate inhibitor composition from said first distillation vessel in liquid form; (f) withdrawing liquid from said first distillation vessel and removing solids therefrom; wherein the withdrawal of steps (e) and (f) may be of a single liquid stream and wherein at least a portion of the lean hydrate inhibitor composition withdrawn from said first distillation vessel is not recycled into said first distillation vessel.

8 Claims, 1 Drawing Sheet

(56) References Cited

U.S. PATENT DOCUMENTS

| | | | |
|---|---|---|---|
| 6,023,003 A * | 2/2000 | Dunning et al. | 568/868 |
| 6,508,916 B1 * | 1/2003 | Razzaghi et al. | 203/11 |
| 2005/0072663 A1 | 4/2005 | Laborie et al. | |

FOREIGN PATENT DOCUMENTS

| | | |
|---|---|---|
| WO | 00/76624 A2 | 12/2000 |
| WO | 2007/073204 A1 | 6/2007 |

* cited by examiner

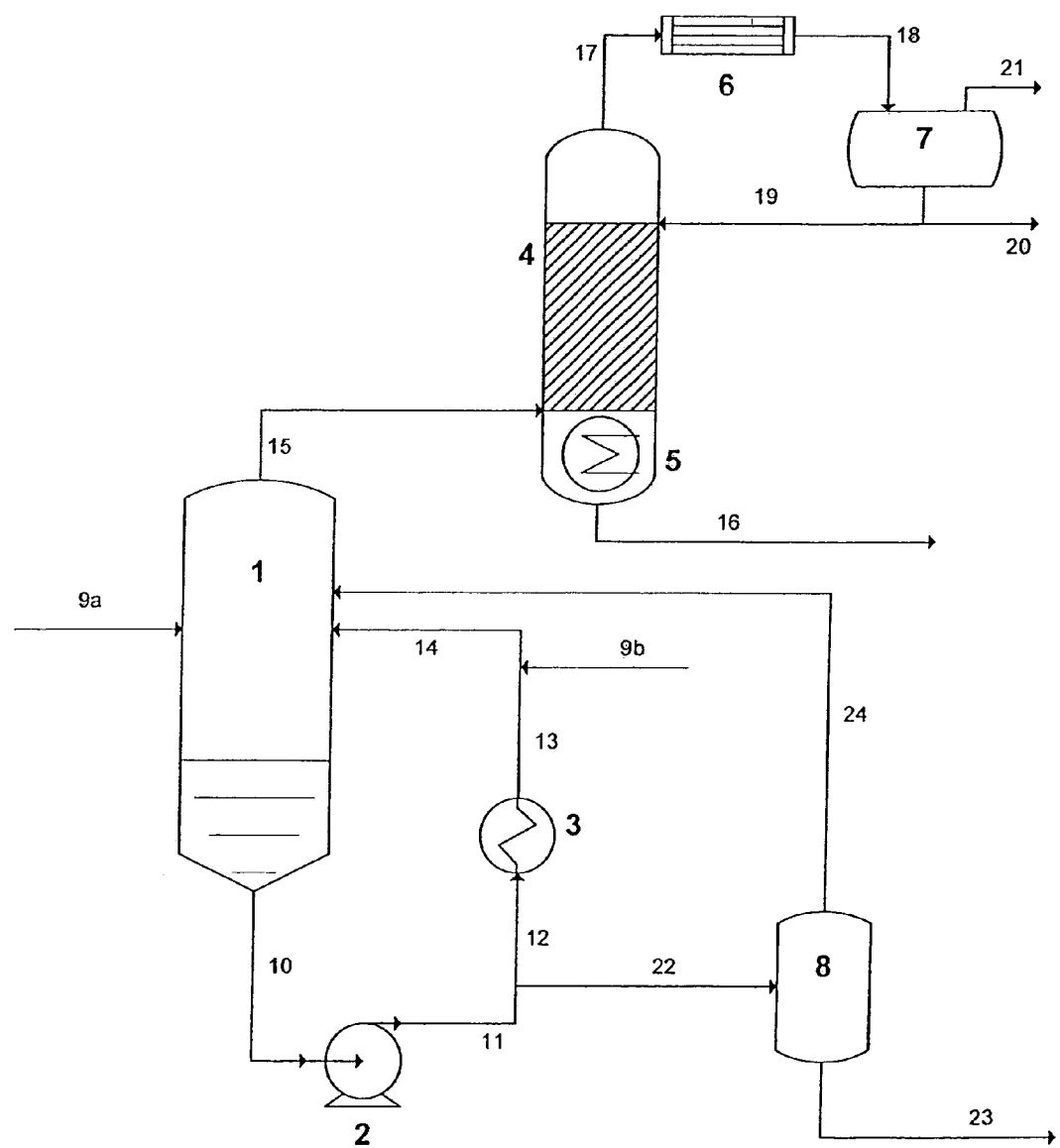

PROCESS FOR HYDRATE INHIBITOR REGENERATION

This invention relates to a process for the regeneration of liquid hydrate inhibitors and to apparatus for use therein.

When unprocessed or partially processed hydrocarbons are transported in a pipeline, for example from a well head, water may be present with the flowing hydrocarbon. If the temperature within the pipeline is low and the pressure is high, the system can enter the hydrate region where gas hydrates form. At 100 bara, the temperature for hydrate formation may be as high as 20° C. At 400 bara, the temperature for hydrate formation may be as high as 30° C. Gas hydrates are solids and behave like ice and if formed in large quantities may plug the pipeline. Hydrates may also plug or cause malfunction of other units, such as valves, chokes, separators, heat exchangers, etc.

There are several methods which may be used to avoid hydrate formation, but in long pipelines, especially sub-sea pipelines, the most common method is to add a liquid hydrate inhibitor which lowers the maximum hydrate formation temperature to below the operating temperature. Various alcohols, glycols, amines and salts have been used as inhibitors and the choice of which inhibitor is to be used depends upon several factors. The most common method for avoiding hydrate formation in pipelines, however, is to inject an alcohol such as methanol or ethanol or a glycol such as monoethylene glycol (1,2-ethanediol or MEG). These are liquid inhibitors which are completely miscible with water. One major difference between the alcohols and the glycols is in their boiling points and vapour pressures. Both methanol and ethanol have a boiling point below 100° C., while MEG, diethyleneglycol (DEG) and triethyleneglycol (TEG) have boiling points well above 100° C. The boiling point of MEG, the most commonly used glycol, is 198° C. As a result, the vapour pressures of the glycols are much lower than those of the lower alcohols and less glycol will be present in the gas phase. For long gas pipelines, the loss of methanol and ethanol to the gas phase would be significant and it is necessary to inject excess alcohol inhibitor in order to retain a satisfactory concentration within the aqueous phase. For gas fields, where the amount of gas is very high compared to the amount of water in the flowing hydrocarbon, glycols, and in particular MEG, are often the preferred inhibitors.

The inhibitor concentration varies with the specific selected inhibitor and how much of it is required to lower the hydrate formation temperature below the pipeline temperature. Typically, the inhibitor will be present as about 30-75% weight of the aqueous phase. The amount of inhibitor that has to be injected is thus dependent on the water content of the hydrocarbon and as the required inhibitor injection rate may be several hundreds of cubic meters per day, for economic, logistic and environmental reasons it is necessary to recover and recycle the inhibitor.

The aqueous phase in a hydrocarbon pipeline can be a complex mixture. The main components are water and the hydrate inhibitor. There will of course also be dissolved hydrocarbons and components from the gas/condensate. As the solubility of most hydrocarbons is low, the main dissolved components are carbon dioxide and light hydrocarbons. The content of some hydrocarbons, especially polar, aromatic and cyclic hydrocarbons, can become quite high due to the presence of the inhibitor. If the gas phase contains hydrogen sulphide, some of this will partition into the aqueous phase. Dissolved carbon dioxide and hydrogen sulphide result in the presence of bicarbonate, carbonate, and bisulphide ions.

Due to corrosion, the aqueous phase will also contain some corrosion products, mainly iron ions and solids such as iron carbonate, iron oxides, etc. The corrosion process will generally also release traces of other components from the metal alloy of the pipeline, for example chromium, copper, manganese, nickel, etc.

Normally, the hydrocarbon flow within the pipeline will also contain some water from the subterranean hydrocarbon reservoir, normally referred to as formation water. This formation water contains various dissolved ions, in particular sodium, chloride, potassium, magnesium, calcium, barium, strontium, iron, sulphate, etc. ions. It is frequently the case that the water phase also contains dissolved organic acids, mainly acetic acid; however the short chain alkanoic acids such as formic, propanoic and butanoic acids are commonly also present.

The aqueous phase within the pipeline can also contain various chemicals used in the production and transportation process, such as corrosion and scale inhibitors, pH stabilizers, drilling fluids, and pipeline conservation fluids.

The aqueous inhibitor phase coming out of the pipeline is referred to as "rich" because it is rich in water. The recovered liquid inhibitor is called "lean" because its water content is lower. Lean liquid hydrate inhibitors generally have a hydrate inhibitor content of 75-100% weight, typically about 90% weight. The rich liquid hydrate inhibitor generally contains about 30-75% weight of the hydrate inhibitor.

The present invention is concerned with the recovery for re-use of lean liquid hydrate inhibitors, where the hydrate inhibitor has a boiling point higher than that of water, for example where the hydrate inhibitor is a glycol such as MEG, DEG or TEG. The invention is concerned particularly with the recovery of lean MEG.

The recovery process is primarily concerned with the removal of water from the rich liquid hydrate inhibitor. In principle this can be achieved by a simple distillation. This can be carried out for MEG for example at about 140-150° C. and 1.1-1.3 bara. Water vapour is drawn off and the lean hydrate inhibitor is drawn off as a liquid. The correct hydrate inhibitor concentration within the withdrawn liquid stream may be obtained by adjusting the temperature or pressure within the reboiler. Under normal operation, with this simple distillation of rich MEG, the MEG concentration in the top product, i.e. the water, is generally well below 500 ppm, sometimes as low as 50-200 ppm.

This simple distillation process is normally referred to as "regeneration".

The regeneration process is sometimes insufficient as it only removes water and dissolved volatiles from the liquid hydrate inhibitor. It doesn't remove dissolved impurities like salts and other compounds with high boiling points. To clean the liquid hydrate inhibitor of such impurities, it is necessary to carry out a further distillation in which the liquid hydrate inhibitor is withdrawn in the gas phase. This is normally done using a distillation vessel operating at reduced pressure, for example a flash separator or reclaimer.

Flash separators normally operate at a pressure of 0.15 to 0.3 bara and at this pressure MEG can be boiled off at 120-135° C.

This vacuum distillation of the hydrate inhibitor is referred to as a reclamation process. When the hydrate inhibitor feed into the reclaimer contains salts, the salt concentration in the liquid in the reclaimer will increase and at some point the salts will begin to precipitate out. Precipitated salts are generally removed by taking liquid from the reclaimer, removing solids and returning the liquid to the reclaimer. The solids removal may be, for example, by filtering, settling or centrifuging.

Where the total flow of rich inhibitor is subjected to reclamation and the water and inhibitor top product is subjected to regeneration, the recovery process is often referred to as a full reclamation and the lean inhibitor product is essentially free of salts and other non-volatiles. However, in the early stages of operation of a hydrocarbon field there is generally very little salt in the rich inhibitor and indeed the salt content may also be kept down by removing any liquid aqueous phase from the flowing hydrocarbon before the inhibitor is added. Accordingly, in some situations it is possible to recover the inhibitor without reclamation or with reclamation being effected on only part of the inhibitor flow upstream or downstream of the regenerator. Such partial reclamation can reduce inhibitor recovery costs, for example by reducing the energy demand or by reducing the quantities of production chemicals (e.g. scale and corrosion inhibitors, pH stabilizers, etc) that must be added to the recovered lean hydrate inhibitor before it is reused.

Nevertheless, regeneration with downstream reclamation and regeneration with upstream reclamation both have drawbacks and the present invention is directed to reducing those drawbacks. Thus we have found that efficiencies in liquid hydrate inhibitor recovery for recycling can be achieved if the recovery process comprises two distillations in series with a lean inhibitor being removed as the bottom product of each distillation. The lean bottom product of the first distillation is a "salty" inhibitor, while that of the second distillation is free of non-volatile impurities. This "clean" lean inhibitor may be reused as such. The "salty" lean inhibitor may require some dilution with clean lean inhibitor or may be subject to a downstream reclamation.

Relative to standard regeneration with downstream reclamation, the process of the invention can reduce the size and energy consumption of the downstream reclaimer significantly, for example about 25%. Relative to standard regeneration with upstream reclamation, clean lean hydrate inhibitor can be produced without having to feed the regeneration unit with clean rich hydrate inhibitor. Thus a suitable recyclable product can be produced more economically and more flexibly.

Thus, viewed from one aspect, the present invention provides a process for the production of a lean liquid hydrate inhibitor composition from a rich liquid hydrate inhibitor composition in which the liquid hydrate inhibitor has a boiling point above that of water, which process comprises:
(a) feeding said rich liquid hydrate inhibitor composition to a first distillation vessel;
(b) withdrawing a water and inhibitor containing vapour from said first distillation vessel and feeding it to a second distillation vessel;
(c) withdrawing water vapour from said second distillation vessel;
(d) withdrawing a lean hydrate inhibitor composition from said second distillation vessel in liquid form;
(e) withdrawing a lean hydrate inhibitor composition from said first distillation vessel in liquid form;
(f) withdrawing liquid from said first distillation vessel and removing solids therefrom;
wherein the withdrawal of steps (e) and (f) may be of a single liquid stream and wherein at least a portion of the lean hydrate inhibitor composition withdrawn from said first distillation vessel is not recycled into said first distillation vessel.

The portion of the lean hydrate inhibitor composition which is not recycled into the first distillation vessel may be the entire stream withdrawn from the first distillation vessel if steps (e) and (f) are of a single liquid stream or the entire stream withdrawn in step (e) if steps (e) and (f) involve withdrawal of two separate streams. Thus a reusable "salty" lean hydrate inhibitor composition may be obtained from the first distillation vessel in addition to the reusable "salt-free" lean hydrate inhibitor composition from the second distillation vessel.

By "distillation vessel" is meant herein a vessel from which a liquid phase stream and a gas phase stream are withdrawn. While the gas phase may be subjected to reflux this is not required and in the first distillation vessel will not generally be done.

In the process of the invention heat sufficient to cause the liquid in the first distillation vessel will generally be introduced within that vessel and/or into liquid in a recirculation loop outside that vessel. The heating may be by way of a heater, e.g. a reboiler, for example in the form of a heater coil heated by electricity or a heated fluid, or alternatively and preferably much if not most of the heating will be by way of heat exchange, e.g. using a heat exchanger disposed outside the vessel, with a hotter fluid from a different stage of the process or from a different process. In particular, it is preferred that liquid removed from the first distillation vessel in steps (e) and/or (f) or in a separate withdrawal and return loop, is used to heat the rich hydrate inhibitor composition feed stream. The rich hydrate inhibitor feed stream may also be injected into the return flow to the distillation vessel upstream, or more preferably downstream, of the solids removal unit used in step (f), and/or upstream or downstream of an external heat exchanger if such is present.

The first distillation vessel may thus conveniently be a reboiler unit.

In the process of the invention, the lean liquid inhibitor composition withdrawn in step (e) is preferably liquid withdrawn downstream of the solids removal in step (f). If it is withdrawn upstream of solids removal in step (f) or if it is removed in a separate liquid stream, it may be necessary to perform a further solids removal process step on this salty lean liquid hydrate inhibitor composition.

In the process of the invention, it is preferred that at least part of the liquid withdrawn in step (f) is returned to the first distillation vessel after the solids removal step.

The composition of the lean hydrate inhibitor composition withdrawn from the first distillation vessel for reuse will be a function of the pressure and temperature in the vessel. The pressure will generally be 0.7 to 2.0 bara, especially 1.0 to 1.5 bara. The temperature will generally be between the boiling points of water and the inhibitor. The pressure will generally be kept as low as possible, typically about 1.1-1.4 bara. For MEG, if the pressure is 1.25 bara and the lean MEG product is to be 90% weight MEG, the temperature in the distillation vessel will generally be about 147° C. Under these conditions, the vapour leaving the first distillation vessel will contain about 29% weight MEG which will condense in the second distillation vessel to produce salt-free lean MEG as the bottom product of the second distillation vessel.

The relative amount of each type of lean liquid hydrate inhibitor composition produced will be a function of the inhibitor concentration in the rich feed. When the inhibitor concentration in the feed is reduced, more of the lean inhibitor can be taken out as salt free lean inhibitor from the second distillation vessel. Thus, for example, if the rich feed contains about 60% weight MEG, then about 25% of the lean MEG can be salt free.

The second distillation column can be a standard distillation column with a reboiler. Once again, any convenient form of reboiler may be used, e.g. an internal heating coil or an external heat exchanger with a recirculation loop. If the top product water vapour is condensed, the distillation can be controlled by water reflux from the condensation unit and heat input from the reboiler so as to get water out of the top and lean inhibitor from the bottom. Non-condensables may be vented, for example, to a VOC or flare system. Water not used for reflux may be sent for water treatment and disposal or for use elsewhere in the process.

It is possible to operate the second distillation vessel without a reboiler; however this gives a very narrow operation window and is not preferred. Introducing a small reboiler unit increases the operation window and the turndown of the column significantly.

The apparatus used for the process of the invention has some similarity to a standard full reclamation unit. However, the first distillation vessel need not be operated under vacuum and a lean inhibitor stream is drawn off from it as a bottom product for reuse. The process of the invention, as described, produces two lean inhibitor products, one salt-free and the other not. This split into two recovered inhibitor products has several important advantages. In particular, the salt-free and salty lean inhibitor products can be mixed either completely or in different ratios to produce different lean inhibitor products. This can be a big advantage when a lean inhibitor is to be injected into different wells or flowlines which require different concentrations of pH stabiliser. The salt-free lean inhibitor product may also be used elsewhere in the process plant where salt-free lean hydrate inhibitor is needed. In this way, the need for separate hydrate inhibitor systems may be reduced or avoided and the logistics of hydrate inhibitor handling may be simplified.

Long pipelines are normally made from carbon steel and in contact with water corrosion will occur. The corrosion rate and type of corrosion depends on the temperature and the composition of the aqueous phase, i.e. pH, salt concentration, carbon dioxide and hydrogen sulphide concentration, etc. Two common methods to avoid corrosion are to add a corrosion inhibitor or to increase the pH by adding a caustic salt, a pH stabiliser, to the inhibitor before it is injected.

A further advantage of the invention is that, as mentioned above, any downstream reclamation unit may be significantly smaller and thus less energy demanding than in a standard system.

By increasing the temperature in the first distillation vessel, the inhibitor concentration in the bottom product of this vessel will increase. Moreover, more inhibitor will go with the water vapour into the second distillation vessel and thus a greater proportion of the overall lean inhibitor product will be clean lean inhibitor. Thus, for example, for a unit processing rich 60% weight MEG at a pressure of 1.25 bara, if the temperature is 147° C. then the proportion of salt-free lean MEG produced will be about 24%. If the temperature is increased to 155° C., then this proportion increases to about 41%.

As more of the lean inhibitor is produced as salt-free lean inhibitor, the salt concentration in the salty lean inhibitor will increase. Thus a smaller amount of salty lean inhibitor has to be processed in order to remove the same amount of salt. By concentrating the salt in the first distillation vessel, the size of any downstream reclamation unit is significantly reduced.

If the temperature in first distillation vessel is further increased, for example to about 170° C. for the case of 60% weight MEG rich feed and 1.25 bara, then substantially all the inhibitor will evaporate and the first distillation vessel will function as a reclaimer. Precipitated solids may then be removed conventionally. In this operation mode, little or no salty lean inhibitor would be withdrawn for reuse as a bottom product from the first distillation vessel. If desired, the apparatus may alternate between periods operating in this mode and periods operating in the reclamation mode.

The apparatus used for inhibitor recovery according to the invention may involve a single first distillation vessel upstream of a single second distillation vessel. However, it is possible to have one or several, preferably several, first distillation vessels leading to one or several, preferably one, second distillation vessels. It is particularly preferred to have several first distillation vessels feeding vapour to a single second distillation vessel. In this event, some of the first distillation vessels may be run as regenerators and some as reclaimers. A very robust and flexible option would be to have 3 first distillation vessels (e.g. with 50% capacity each) and one second distillation vessel with 100% capacity, e.g. 3 reboilers and one distillation column, as most of the process upsets that may occur are likely to occur in the reboilers. With this option, it would not be necessary to have back-up circulation pumps and heat exchangers on each reboiler as there would be one standby reboiler.

A common rule of thumb during MEG regeneration is that the MEG should not be heated above 165° C. in order to avoid degradation into different organic acids and other compounds. As the degradation reaction to form acids is an oxidation, it can be avoided by removing oxygen from the feed and apparatus. One of the major problems with the current reclaimers however is that they work under vacuum and there will generally be a small leakage of air into the reclaimer. Using the process of the invention, the need to operate under vacuum can be avoided.

Improvements realised with the process according to the invention as compared with traditional processes include the following:

(i) as there is no salty rich inhibitor in the distillation column, salt precipitation and scale formation in the distillation column and the column packing is avoided, (ii) the first distillation vessel may simply be a reboiler designed, like a reclaimer unit, to handle possible solids, (iii) the reflux of the distillation column is normally sent back to the reboiler but with the process of the invention it is possible to produce salt free lean inhibitor without a desalting unit, (iv) by introducing a small reboiler into the distillation column of the second distillation vessel, the reflux rate can be increased to reduce inhibitor concentration in the overhead water and it is possible to obtain a turndown close to 100% by not draining inhibitor and running 100% reflux. The distillation column can be kept in operation with no feed from the reboiler, (v) the process of the invention gives two lean inhibitor products, one salt free and the other salty. This can be an advantage if salt free inhibitor is to be used for other purposes. Moreover, the fraction of salt free lean inhibitor can be increased or decreased as desired, (vi) compared to traditional designs, the salty lean inhibitor stream is saltier but smaller. This means that any downstream de-salting unit will also be smaller, (vii) by increasing the temperature in the first distillation vessel, more of the lean inhibitor can be produced as salt free lean inhibitor from the second distillation vessel. The salty lean inhibitor from the first distillation vessel will then have a higher inhibitor concentration although with a higher salt concentration. If the salty lean inhibitor from the first distillation vessel is then subject to downstream reclamation, the downstream reclamation unit may be far smaller than normal, (viii) by increasing the temperature in the first distillation vessel, it may be transformed from operating as a regenerator into operating as a reclaimer. By periodically running in reclamation mode, salt can be removed and the need for a downstream reclamation unit can be avoided, and (ix) by running the distillation vessels at near atmospheric pressure, preferably slightly above atmospheric pressure, the units can be significantly smaller and lighter (as compared with conventional full reclamation systems) and air leakage and oxygen contamination can be avoided. Moreover, the vent gas will be oxygen free and so can be vented to a flare system.

(x) by running an upstream partial desalting unit, it is nonetheless possible to produce salt-free lean hydrate inhibitor. With a conventional regeneration unit, this would require the use of a salt-free rich inhibitor feed.

As is conventional for hydrate inhibitor recovery, the flow to the recovery apparatus may first be subjected to oil/water and water/gas separation steps.

Viewed from a further aspect, the present invention provides apparatus for recovery of a lean liquid hydrate inhibitor composition from a rich liquid hydrate inhibitor composition, said apparatus comprising a first distillation vessel and a second distillation vessel connected in series, said first distillation vessel and said second distillation vessel being connected by a conduit permitting transfer of vapour from said first distillation vessel to said second distillation vessel, said second distillation vessel having a port for removal of a lean liquid hydrate inhibitor composition in liquid form and a port for removal of water vapour, and said first distillation vessel having a port for removal without return of a liquid lean hydrate inhibitor composition and having a solids removal unit for removal of solids from liquid therein.

In the apparatus to the invention, the first distillation vessel is preferably provided with a withdrawal and return loop containing a said solids removal unit and from which said lean liquid hydrate inhibitor composition may be withdrawn, preferably downstream of said solids removal unit.

The process and apparatus of the invention will now be described further with reference to the accompanying drawing in which:

FIG. 1 is a schematic diagram of an apparatus according to the invention.

Referring to FIG. 1 there is shown a first distillation vessel 1 in the form of a reboiler with an external heat exchanger 3 and a liquid circulation loop provided by conduits 10 to 14. First distillation vessel 1 is connected to a second distillation vessel 4 by vapour conduit 15. Second distillation vessel 4 is in the form of a distillation column having a reboiler 5. From the base of the second distillation vessel 4, salt free lean inhibitor may be withdrawn through conduit 16. From the top of the second distillation vessel 4, water vapour is withdrawn through conduit 17 and fed to condenser 6 and thence through conduit 18 to reflux drum 7. The condenser 6 may also be integrated in the top of the distillation column 4. Non-condensables are vented from drum 7 through conduit 21 and water is withdrawn from drum 7 and returned to cool the second distillation vessel 4 through reflux line 19 or sent for further processing via conduit 20.

Liquid from the base of the first distillation vessel 1 is withdrawn through conduit 10 and recycled through a circulation pump 2 via conduits 11 and 12 to the heat exchanger 3. This heat exchanger provides the liquid re-entering vessel 1 with sufficient heat to boil there. The heated salty inhibitor is fed back into the first distillation vessel 1 via conduits 13 and 14. Conduit 22 leads to a solids removal unit 8 and a salty lean hydrate inhibitor composition may be removed from solids removal unit 8 via conduit 23. If desired, this salty lean product may be subjected to reclamation. Conduit 9a provides a direct feed into the first distillation vessel while conduit 9b allows the rich feed to be introduced into the recycle loop. Conduit 9b preferably is downstream of the heat exchanger 3 in order to reduce the possibility of salt precipitation in the heat exchanger. If salt precipitation or scale formation is not expected, the preferred injection point for the rich feed would be upstream of heat exchanger 3. If the first distillation vessel 1 is operated in full reclamation mode, all of the liquid from solids removal unit 8 is returned into vessel 1 via conduit 24.

The invention claimed is:

1. A process for the production of a lean liquid hydrate inhibitor composition and a reusable salty lean hydrate inhibitor composition from a rich liquid hydrate inhibitor composition in which the liquid hydrate inhibitor has a boiling point above that of water, the process comprising:
   (a) feeding said rich liquid hydrate inhibitor composition to a first distillation vessel;
   (b) withdrawing a water and inhibitor containing vapor from said first distillation vessel and feeding it to a second distillation vessel;
   (c) withdrawing water vapor from said second distillation vessel;
   (d) withdrawing said lean hydrate inhibitor composition which is free of non-volatile impurities from said second distillation vessel in liquid form;
   (e) withdrawing said salty lean hydrate inhibitor composition from said first distillation vessel in liquid form; and
   (f) withdrawing liquid from said first distillation vessel and removing solids therefrom;
   wherein the withdrawal of (e) and (f) may be of a single liquid stream and wherein the entire salty stream withdrawn from the first distillation vessel in step (e) is not recycled into said first distillation vessel.

2. The process as claimed in claim 1 wherein said liquid hydrate inhibitor is monoethylene glycol.

3. The process as claimed in claim 1 wherein vapor from a plurality of first said distillation vessels is fed to a single second said distillation vessel.

4. The process as claimed in claim 1 wherein temperature of the first distillation vessels is operated in a range to produce a varying feed composition to the second distillation vessel.

5. The process as claimed in claim 1 wherein the withdrawal of (e) and (f) are of a single liquid stream.

6. The process as claimed in claim 1 wherein steps (e) and (f) involve withdrawal of two separate streams.

7. The process as claimed in claim 1 wherein the lean liquid inhibitor composition withdrawn in step (e) is liquid withdrawn downstream of the solid removal step in step (f).

8. The process as claimed in claim 1 wherein at least part of the liquid withdrawn in step (f) is returned to the first distillation vessel after the solids removal step.

* * * * *